United States Patent [19]

Gauthier-Lafaye et al.

[11] 4,436,889

[45] Mar. 13, 1984

[54] PREPARATION OF CARBOXYLIC ACIDS BY CARBONYLATION OF ALCOHOLS

[75] Inventors: Jean Gauthier-Lafaye, Lyons; Robert Perron, Charly, both of France

[73] Assignee: Rhone-Poulenc Industries, Paris, France

[21] Appl. No.: 260,810

[22] Filed: May 5, 1981

[30] Foreign Application Priority Data

May 6, 1980 [FR] France ............................ 80 10540

[51] Int. Cl.$^3$ ..................... C07C 51/12; C07C 53/08; C07C 53/134; C07C 57/30; C07C 57/32
[52] U.S. Cl. ................................. 562/519; 560/232; 562/406; 562/497; 562/517
[58] Field of Search ............... 562/519, 406, 497, 517, 562/520, 521; 560/232, 114, 204; 260/413

[56] References Cited

U.S. PATENT DOCUMENTS 2,650,245 8/1953 Thomas et al. ..................... 562/519
4,133,963 1/1979 Holmes .............................. 562/519

FOREIGN PATENT DOCUMENTS 2749955 5/1978 Fed. Rep. of Germany ...... 562/519

*Primary Examiner*—Vivian Garner
*Attorney, Agent, or Firm*—Burns, Doane, Swecker & Mathis

[57] ABSTRACT

Carboxylic acids having the structural formula $R^1COOH$, wherein $R^1$ is a linear, branched or cyclic chain alkyl radical of from 1 to 6 carbon atoms or a phenyl-$C_nH_{2n}$-radical wherein $1 \leq n \leq 6$, are prepared by carbonylating an alcohol having the formula $R^1$-OH with carbon monoxide in liquid phase, in the presence of a catalytically effective amount of nickel and an alkyl or acyl halide promoter therefor, at a temperature of at least about 120° C. and under a total pressure of less than 200 bars, and said carbonylation being carried out in the presence of at least one vanadium compound in which the vanadium is in an oxidation state of 4 or 5, and in an initial carboxylic acid reaction medium having the formula $R^2$-COOH, wherein $R^2$ is defined as was $R^1$ above, and further wherein $R^1$ and $R^2$ may be the same or different.

21 Claims, No Drawings

PREPARATION OF CARBOXYLIC ACIDS BY CARBONYLATION OF ALCOHOLS

CROSS-REFERENCE TO RELATED APPLICATIONS

Our copending applications, Ser. No. 235,742 filed Feb. 18, 1981; Ser. No. 247,744, filed Mar. 26, 1981, now U.S. Pat. No. 4,351,953; and Ser. No. 260,811, filed concurrently herewith, all assigned to the assignee hereof, and all hereby expressly incorporated by reference and relied upon.

BACKGROUND OF THE INVENTION

1. Field of the Invention

The present invention relates to the preparation of carboxylic acids, and, more especially, to the preparation of carboxylic acids, notably acetic acid, by carbonylation of an alcohol.

2. Description of the Prior Art

It is well known to this art that, e.g., acetic acid, can be prepared by carbonylation of methanol under relatively severe reaction conditions of pressure, in the presence of nickel and a free or bound halogen.

Thus, it has been proposed, in particular (compare U.S. Pat. No. 2,729,651), to carry out the carbonylation of methanol in the presence of nickel complexes which are obtained by reacting nickel halides with quaternary ammonium (or phosphonium) halides, i.e., complexes of the general formula:

$$[A_4M]_2NiX_4$$

in which X represents a bromine or iodine atom, M represents a phosphorus or nitrogen atom and A is, for example, a lower alkyl radical.

These complexes can be used in the aforesaid form in the reaction in question, or they can be formed in situ. However, although increased pressure (on the order of 700 atmospheres) is applied during the carbonylation reaction, the efficiency of the catalyst system, expressed in terms of hourly output or yield, is very low.

It has been possible to substantially improve this output, expressed either with respect to the reaction volume or with respect to the amount of nickel used, by employing in the subject reaction a nickel halide, on the one hand, and, on the other hand, a quaternary ammonium (or phosphonium) halide in a quantity greater than that required by the stoichiometry of formation of the complexes of the aforenoted formula. Compare German Pat. No. 933,148. However, in this latter case, the pressure conditions remain severe.

More recently, catalyst systems which permit the carbonylation of methanol under less severe conditions of pressure have been proposed. Thus, published French Patent Application No. 2,370,023 describes the carbonylation of methanol in the presence of at least 10 mols of methyl iodide per 100 moles of methanol, and in the presence of nickel and of a free phosphine and/or a phosphine complexed with the nickel, under a pressure of less than 70 bars. However, the efficiency of such a system, again expressed in terms of hourly output, remains low.

In the context of a carbonylation process under low pressure, it has also been emphasized (compare published French Patent Application No. 2,404,618) that the presence of solvents, such as carboxylic acids or their esters, has a favorable effect on the course of the carbonylation reaction. However, utilization of such solvents is not essential, and the starting material alcohol can also serve as the solvent.

However, the industrial or commercial value of these recent developments is limited as a result of the instability and the cost of the phosphines or of the amines required to effect these techniques.

SUMMARY OF THE INVENTION

Accordingly, a major object of the present invention is the provision of an improved process for the preparation of carboxylic acids, notably alkanoic acids, and especially acetic acid, such improved process being characterized by markedly enhanced output, by carbonylation of alcohols in the presence of nickel and at least one halogen-containing promotor under reaction conditions of relatively mild pressure, and such process being conspicuously devoid of the aforenoted disadvantages and drawbacks.

Briefly, the present invention features an improved process for the carbonylation of alcohols in liquid phase, under a total pressure of less than 200 bars, in the presence of a catalytically effective amount of nickel, an alkyl or acyl halide and at least one vanadium compound wherein the vanadium is in an oxidation state of 4 or 5, and a beginning amount of a carboxylic acid.

DETAILED DESCRIPTION OF THE INVENTION

More particularly according to this invention, it has now surprisingly been found that, e.g., the carbonylation of methanol in acetic acid proceeds quite satisfactorily when the partial pressure of the carbon monoxide is maintained relatively low; this is all the more unexpected since the state of this art has to date clearly pointed to the necessity for carrying out the carbonylation under very high pressure.

Even more particularly, the focus of the present invention is the demonstrated surprising activity of those vanadium compounds in which the vanadium is in an oxidation state of 4 or 5, when used as co-catalysts, in the carbonylation of an alcohol, in liquid phase, under a total pressure of less than 200 bars. Indeed, it has even been confirmed that the salts and other derivatives of numerous metals (including metal carbonyls) do not permit the reaction of carbon monoxide with an alcohol in a carboxylic acid medium under the aforesaid reaction conditions, in the presence of nickel and a halogen-containing promoter.

According to the present invention, carbon monoxide is reacted with an alcohol in order to produce the corresponding carboxylic acid, in accordance with the following equation:

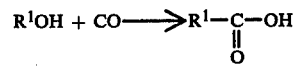

in which $R^1$ represents a linear, branched or cyclic alkyl radical containing from 1 to 6 carbon atoms, or a radical phenyl-$C_nH_{2n}$-, in which n is an integer ranging from 1 to 6 ($1 \leq n \leq 6$). The radical $R^1$ can also bear one or more substituents which are inert under the reaction conditions of the present invention. $R^1$ is preferably a linear or branched chain lower alkyl radical having from 1 to 4 carbon atoms, and more preferably is a methyl radical.

The process according to the present invention is carried out in the liquid phase in a reaction medium comprising a carboxylic acid of the formula $R^2COOH$, in which $R^2$ is defined exactly as was $R^1$, it thus being possible for $R^2$ and $R^1$ to either be the same or different. Expressed otherwise, the carboxylic acid which, so to speak, functions as a solvent is not necessarily the particular carboxylic acid produced by the carbonylation reaction. However, it may indeed prove preferable for the carboxylic acid employed as the solvent to be that produced in the reaction. Needless to say, employing as the solvent a carboxylic acid which is heavier than the acid produced can facilitate the separation operation.

The carboxylic acid $R^2COOH$ advantageously constitutes at least 10% by volume of the initial reaction mixture. It preferably constitutes at least 20% by volume of said reaction mixture. It can constitute a substantial proportion of the reaction mixture, especially in the case of an operation carried out continuously, by injecting the alcohol $R^1OH$ into the carbonylation reactor.

The process according to the invention requires the presence of a catalytically effective amount of nickel. Any source of nickel can be used within the scope of the present process. Thus, it is possible to introduce the nickel in its metallic form (for example Raney nickel) or in any other convenient form. Examples which are exemplary of nickel compounds which can be utilized for carrying out the present process are: the carbonate, oxide, hydroxide, halides, in particular the iodide, and carboxylates, in particular the acetate, of nickel. Nickel carbonyl is also particularly suitable. Raney nickel, nickel iodide, nickel acetate and nickel carbonyl are preferred to be used.

The amount of nickel is not critical. The proportion of nickel which affects the rate of reaction is determined as a function of the rate of reaction calculated as suitable. In general, an amount of nickel between 5 and 2,000 milligram-atoms per liter of solution gives satisfactory results. The reaction is preferably carried out with an amount of nickel between 20 and 1,000 milligram-atoms per liter.

The process according to the present invention also requires the presence of at least one alkyl or acyl halide. The formulae of these halides are, respectively, $R^3X$ and

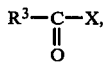

in which X represents a chlorine or bromine atom, or, preferably, an iodine atom and $R^3$ is defined exactly as was $R^1$ (and $R^2$), it being possible for $R^3$ and $R^1$ (or $R^3$ and $R^2$) to be identical or different. The alkyl halide which can initially be used in the reaction mixture can, of course, be formed in situ, starting from halogen derivatives, such as $Cl_2$, $Br_2$, $I_2$, HCl, HBr, HI, $NiBr_2$ and $NiI_2$, and from the alcohol (starting material). Stated differently, some or all of the alkyl halide required for carrying out the present process can be formed starting from its "precursors" defined above.

Furthermore, it will be noted that when the halogen derivative is selected from among the nickel compounds, it can be considered not only as a precursor of the alkyl halide but also as a precursor of the metallic catalyst. In this particular case, it is also preferred to add, initially, an alkyl or acyl halide and/or a precursor other than the nickel halides in question.

Within the ambit of the present invention, lower alkyl iodides having from 1 to 4 carbon atoms define a preferred class of alkyl halides. Methyl iodide is particularly suitable for carrying out the process according to the invention.

An alkyl or acyl halide concentration of at least 0.5 mol per liter of reaction mixture is typically required for successfully carrying out the present process. Although increasing the concentration of alkyl or acyl halide has a favorable effect on the rate of reaction, it is preferred not to exceed a concentration on the order of 8 mols per liter. For this reason, a concentration of alkyl or acyl halide between 0.8 and 6 mols/liter, and preferably between 1.5 to 5 mols/liter provides satisfactory results.

One of the essential characteristics of the present invention is the use of at least one vanadium compound in which the vanadium is in an oxidation state of 4 or 5, namely, of at least one compound selected from the group comprising the oxides, the halides and the oxyhalides of vanadium (IV) or vanadium (V) and vanadyl bis-acetylacetonate. The following are exemplary of vanadium compounds which are suitable for carrying out the present process: $VCl_4$, $VOCl_2$, $VOBr_2$, $VO(acac)_2$, $V_2O_5$, $VOCl_3$ and $VOBr_3$.

From among the vanadium (IV) compounds, vanadyl bis-acetylacetonate $[VO(acac)_2]$ is especially preferred according to the present invention and from among the vanadium (V) compounds, vanadium pentoxide ($V_2O_5$) is the preferred.

Good results are obtained if the atomic ratio V/Ni is between 0.1 and 100, although lower or higher ratios can be selected. This ratio is advantageously a value ranging from 0.2 to 50 and preferably ranging from 0.5 to 25.

A reaction temperature of at least 120° C. is typically required in order to obtain a satisfactory rate of reaction. A temperature range of from 160° to 220° C. proves advantageous.

According to the present invention, it is not necessary to purify or dry the alcohol and the carboxylic acid initially used in the reaction. Technical grade alcohols and carboxylic acids optionally containing up to 20% by volume of water can be utilized. On the other hand, some or all of the alcohol $R^1OH$ can be employed in the reaction in the form of an ester $R^2COOR^1$, $R^1$ and $R^2$ being as defined above and it being possible for $R^1$ and $R^2$ to be identical or different. In this case, an amount of water at least equal to the amount theoretically required to hydrolyze the ester initially introduced should also initially be used.

The carbonylation process according to the present invention is carried out in the liquid phase under a pressure greater than atmospheric pressure, the pressure being, however, less than 200 bars. More particularly, it is recommended to carry out the reaction under a partial pressure of carbon monoxide of between 10 and 100 bars. The carbon monoxide is preferably employed in an essentially pure form, such as is commercially available. However, the presence of impurities, such as, for example, carbon dioxide, oxygen, methane and nitrogen, is not harmful. The presence of hydrogen, even in relatively large proportions, likewise is not harmful.

Upon completion of the reaction, the reaction mixture is separated into it various constituents by any appropriate means, for example, by distillation.

The process according to the invention is particularly suitable for the preparation of acetic acid by carbonylation of methanol, especially in an acetic acid reaction medium.

In order to further illustrate the present invention and the advantages thereof, the following specific examples are given, it being understood that same are intended only as illustrative and in nowise limitative.

The following symbols and definitions have been used in the said examples:
AcOH designates acetic acid;
AcOMe designates methyl acetate;
RY designates the molar ratio:

$$\frac{(AcOH + AcOMe) \text{ determined} - \text{initial } (AcOH)}{\text{initial } (CH_3OH + CH_3I)},$$

i.e., the molar ratio between the "potential acetic acid" formed and the initial $(CH_3OH+CH_3I)$;

t denotes the effective duration of the absorption of the carbon monoxide at the temperature of the experiment; and Pr denotes the productivity or output, relative to the time t (expressed in hours), in grams of "potential acetic acid" formed per liter of the initial reaction mixture.

EXAMPLE 1

The following ingredients were introduced into a Hastelloy B 2 autoclave of 125 ml capacity:
(i) 407 mmols of methanol, i.e. 17 ml;
(ii) 394 mmols of acetic acid, i.e., 23 ml;
(iii) 131 mmols of methyl iodide, i.e., 8 ml;
(iv) 10 mg atoms of vanadium in the form of vanadyl bis-acetylacetonate, i.e., 2.65 g; and
(v) 8 mmols of nickel acetate tetrahydrate, i.e., 2 g.

After closing the autoclave, a pressure of 40 bars of carbon monoxide was established therein. Shaking by means of a reciprocating system was commenced and the autoclave was heated to 200° C., over the course of about 20 minutes, by means of an annular furnace. The pressure in the autoclave was then 68 bars; same was subsequently maintained at 70 bars by introduction of additional amounts of pure CO.

The absorption of carbon monoxide was complete after a reaction time of 75 minutes at 200° C.; heating was nevertheless continued for an additional 45 minutes at this temperature.

The shaking and heating were then stopped; the autoclave was cooled and degassed.

After dilution, the resulting reaction mixture was analyzed by gas chromatography. Same contained 44.3 g of acetic acid (RY=64%). No methyl acetate was detected.

The productivity (Pr) of the reaction in terms of acetic acid was therefore 330 grams per hour and per liter (g/hour×liter).

EXAMPLES 2 TO 9

Using the equipment and the procedure described in Example 1, a series of experiments was carried out on a charge comprising methanol, acetic acid, nickel and, unless otherwise indicated, methyl iodide and vanadyl bis-acetylacetonate. The total duration of the experiment was 2 hours, unless stated otherwise.

The particular conditions and also the results obtained are reported respectively in Tables I (a) and I (b) below.

Control experiment (a), also reported in the tables, was carried out in the absence of vanadium.

Control experiment (b), also reported in the tables, was carried out on a charge containing no acetic acid.

Control experiments (c) to (n)

Using the equipment and the procedure described for Example 1, a series of experiments was carried out on a charge comprising 15 ml of methanol, 20 ml of acetic acid and methyl iodide, at 180° C. and under 70 bars of pressure, in the presence of various metal compounds. No reaction was observed after 2 hours at the temperature indicated.

The particular conditions of these control experiments are reported in Table II below.

EXAMPLE 10

Using the equipment and the procedure described for Example 1, an experiment was carried out on a charge comprising 25 ml (232 mmols) of benzyl alcohol, 15 ml of acetic acid, 161 mmols of methyl iodide, 8 mg atoms of nickel in the form of nickel acetate tetrahydrate and 40 mg atoms of vanadium in the form of vanadyl bis-acetylacetonate. The reaction temperature was 180° C.; the total pressure was maintained at 60 bars by introduction of additional amounts of pure CO. In a reaction time of 1 hour, 30 minutes at the temperature indicated, 15.8 g of phenylacetic acid were obtained (RY=48%).

EXAMPLE 11

Example 1 above was repeated, but 40 mmols of potassium iodide were added to the charge. The absorption of carbon monoxide was complete after a reaction time of 90 minutes at 200° C.; heating was nevertheless continued for 30 minutes at this temperature. The total duration of the experiment was therefore 2 hours. 45.6 g of acetic acid were then determined; no methyl acetate was detected. (RY=69% and Pr=300 g/hour×liter).

TABLE I(a)

| Example No. | MeOH (ml) | AcOH (ml) | CH$_3$I (mmols) | NICKEL COMPOUND type | NICKEL COMPOUND mg atoms | Vanadium mg atoms | Temperature (°C.) | Total pressure (bars) |
|---|---|---|---|---|---|---|---|---|
| 1 | 17 | 23 | 131 | Ni(OAc)$_2$ | 8 | 10 | 200 | 70 |
| 2 | " | " | 130 | NiI$_2$ | " | 20 | 190 | 150 |
| 3 | " | " | 129 | " | " | " | " | 35 |
| 4 | " | " | " | Ni(OAc)$_2$ | 40 | 10 | 180 | 70 |
| 5(x) | 15 | 20 | 202 | " | 8 | 40 | " | " |
| 6 | " | " | " | " | " | 40 | " | " |
| 7 | 20 | 20 | 160 | " | " | 23 | " | " |
| 8 | 19 | 26 | 40 | " | " | 40 | 200 | " |
| 9(xx) | 12 | 30 | 40 | " | " | 25 | 180 | " |
| a | 15 | 20 | 249 | Ni(CO)$_4$ | 20 | 0 | 180 | " |

TABLE I(a)-continued

| Example No. | MeOH (ml) | AcOH (ml) | CH$_3$I (mmols) | conditions NICKEL COMPOUND type | mg atoms | Vanadium mg atoms | Temperature (°C.) | Total pressure (bars) |
|---|---|---|---|---|---|---|---|---|
| b | 45 | 0 | 80 | Ni(OAc)$_2$ | 8 | 39.5 | 200 | " |

N.B.: in this table, Ni(OAc)$_2$ in fact denotes nickel acetate tetrahydrate, and NiI$_2$ in fact denotes NiI$_2$.8H$_2$O.
(x): experiment carried out with 40 mg atoms of vanadium in the form of V$_2$O$_5$ total duration = 2 hours, 35 minutes.
(xx): experiment carried out with 40 mmols of iodine (instead of CH$_3$I) and under a hydrogen partial pressure of 30 bars.

TABLE I(b)

| Example No. | t minutes | results AcOH determined (g) | AcOMe (g) | RY % | Pr g/hour × liter |
|---|---|---|---|---|---|
| 1 | 75 | 44.3 | 0 | 64 | 330 |
| 2 | 120 | 16.0 | 10.2 | 2 | 3 |
| 3 | " | 23.9 | 8.2 | 22 | 70 |
| 4 | " | 32.1 | 8.6 | 49 | 160 |
| 5 | 155 | 36.1 | 4.8 | 55 | 150 |
| 6 | 50 | 44.4 | 0 | 69 | 590 |
| 7 | 120 | 40.0 | 2.9 | 58 | 220 |
| 8 | " | 17.9 | 16.3 | 12 | 40 |
| 9 | " | 45.8 | 0 | 87 | 150 |
| a | — | 10.50 | 10.6 | 0 | 0 |
| b | — | ND | ND | ND | ND |

—: no absorption of carbon monoxide was observed
ND: not determined

TABLE II

| Control Experiment No. | Control experiments NICKEL COMPOUND Type | mg atoms | CH$_3$I in mmols | METAL COMPOUND Type | mg atoms |
|---|---|---|---|---|---|
| c | Ni(CO)$_4$ | 20 | 201 | Cr(CO)$_6$ | 50 |
| d | Ni(CO)$_4$ | 20 | 206 | Zn(OAc)$_2$.2H$_2$O | 100 |
| e | Ni(CO)$_4$ | 20 | 203 | Zn | 50 |
| f | Ni(CO)$_4$ | 20 | 209 | Mn(OAc)$_2$.4H$_2$O | 100 |
| g | Ni(CO)$_4$ | 20 | 204 | AlI$_3$ | 50 |
| h | Ni(CO)$_4$ | 20 | 203 | Co(OAc)$_2$.4H$_2$O | 100 |
| i | Ni(OAc)$_2$.4H$_2$O | 10 | 205 | MoBr$_3$ | 30 |
| j | Ni(OAc)$_2$.4H$_2$O | 8 | 202 | Fe(OAc)$_2$ | 100 |
| k | Ni(CO)$_4$ | 20 | 205 | MoI$_3$ | 10 |
| l | Ni(CO)$_4$ | 10 | 209 | WI$_3$ | 10 |
| m | Ni(CO)$_4$ | 20 | 211 | Mg(OAc)$_2$.4H$_2$O | 100 |
| n | Ni(CO)$_4$ | 8 | 200 | BiI$_3$ | 40 |

The principles, preferred embodiments and modes of operation of the present invention have been described in the foregoing specification. The invention which is intended to be protected herein, however, is not to be construed as limited to the particular forms disclosed, since these are to be regarded as illustrative rather than restrictive. Variations and changes may be made by those skilled in the art without departing from the spirit of the invention.

What is claimed is:

1. A process for the preparation of a carboxylic acid having the structural formula R$^1$COOH, wherein R$^1$ is a linear, branched or cyclic chain alkyl radical of from 1 to 6 carbon atoms or a phenyl-C$_n$H$_{2n}$-radical wherein $1 \leq n \leq 6$, comprising carbonylating an alcohol having the formula R$^1$—OH with carbon monoxide in liquid phase, in the presence of a catalytically effective amount of nickel and an alkyl or acyl halide promoter therefor, at a temperature of at least 120° C. and under and total pressure of less than 200 bars, said carbonylation being carried out in the presence of at least one vanadium compound in which the vanadium is in an oxidation state of 4 or 5, and in an initial carboxylic acid reaction medium having the formula R$^2$—COOH, wherein R$^2$ is defined as was R$^1$ above, and further wherein R$^1$ and R$^2$ may be the same or different.

2. The process as defined by claim 1, wherein the alkyl or acyl halide is an iodide.

3. The process as defined by claim 2, wherein the halide is a C$_1$-C$_4$-alkyl iodide.

4. The process as defined by claim 3, wherein the alkyl iodide is methyl iodide.

5. The process as defined by any of claims 1 to 4, wherein R$^1$ is a C$_1$-C$_4$-alkyl radical and R$^2$ is a linear, branched or cyclic chain C$_1$-C$_6$-alkyl radical or a phenyl-C$_n$H$_{2n}$-radical, in which $1 \leq n \leq 6$.

6. The process as defined by claim 5, wherein R$^1$ is methyl.

7. The process as defined by claim 1, wherein the carboxylic acid R$^2$COOH comprises at least 10% by volume of the initial reaction medium.

8. The process as defined by claim 7, wherein the concentration of nickel in the reaction medium ranges from 5 to 2,000 mg-atoms per liter.

9. The process as defined by claim 8, wherein said concentration of nickel ranges from 20 to 1,000 mg-atoms per liter of reaction medium.

10. The process as defined by claim 8, wherein the concentration of alkyl or acyl halide in the reaction medium ranges from 0.5 to 8 mols per liter.

11. The process as defined by claim 10, wherein said concentration of alkyl or acyl halide ranges from 0.8 to 6 mols per liter.

12. The process as defined by claim 1 or 10, wherein R$^1$ and R$^2$ are identical.

13. The process as defined by claim 1 or 10, wherein the vanadium compound is an oxide, halide or oxyhalide of vanadium (IV) or vanadium (V), or vanadyl bis-acetylacetonate.

14. The process as defined by claim 13, wherein the vanadium compound is VCl$_4$, VOCl$_2$, VOBr$_2$, VO(acetylacetonate)$_2$, V$_2$O$_5$, VOCl$_3$ and VOBr$_3$.

15. The process as defined by claim 14, wherein the vanadium compound is vanadyl bis-acetylacetonate.

16. The process as defined by claim 14, wherein the vanadium compound is $V_2O_5$.

17. The process as defined by claim 13, wherein the atomic ratio V/Ni, ranges from 0.1 to 100.

18. The process as defined by claim 17, wherein the ratio V/Ni ranges from 0.2 to 50.

19. The process as defined by claim 18, wherein the ratio V/Ni ranges from 0.5 to 25.

20. The process as defined by claim 1, wherein the reaction temperature ranges from 160° to 220° C.

21. The process as defined by claim 20, wherein the partial pressure of the carbon monoxide ranges from 10 to 100 bars.

* * * * *